United States Patent [19]

Manus et al.

[11] Patent Number: 4,576,179
[45] Date of Patent: Mar. 18, 1986

[54] RESPIRATION AND HEART RATE MONITORING APPARATUS

[76] Inventors: Eugene A. Manus, 1005 Kentwood Dr., Blacksburg, Va. 24060; Paris H. Wiley, 1907 Ceder Brooke Dr., Lutz, Fla. 33549

[21] Appl. No.: 492,056

[22] Filed: May 6, 1983

[51] Int. Cl.$^4$ .............. A61B 5/08; A61B 5/04
[52] U.S. Cl. .................. 128/671; 128/721; 128/644; 128/700; 338/6
[58] Field of Search ............ 128/670–671, 128/721–722, 774, 782, 639–641, 643–644, 687, 689–690, 700, 714; 73/720–721, 726–727; 338/2, 6

[56] References Cited

U.S. PATENT DOCUMENTS

| | | | |
|---|---|---|---|
| 3,572,317 | 3/1971 | Wade | 128/671 |
| 3,724,274 | 4/1973 | Millar | 128/675 |
| 3,782,368 | 1/1974 | Reibold | 128/687 |
| 3,976,052 | 8/1976 | Junginger et al. | 128/671 |
| 3,995,247 | 11/1976 | Kurtz | 338/6 X |
| 4,047,144 | 9/1977 | Wong | 338/6 X |
| 4,169,462 | 10/1979 | Strubé | 721/128 |
| 4,296,757 | 10/1981 | Taylor | 128/721 |
| 4,305,400 | 12/1981 | Logan | 128/670 |
| 4,306,567 | 12/1981 | Krasner | 128/721 X |
| 4,379,460 | 4/1983 | Judell | 128/671 |
| 4,422,458 | 12/1983 | Kravath | 128/671 |

FOREIGN PATENT DOCUMENTS

1492875  11/1977  United Kingdom ........ 128/721

Primary Examiner—Lee S. Cohen
Assistant Examiner—Angela D. Sykes
Attorney, Agent, or Firm—Arthur W. Fisher, III

[57] ABSTRACT

A respiration and heart rate monitoring apparatus includes a mechanical-electric apparatus for detecting chest movements and electrodes for detecting electric impulses associated with heartbeat. A highly sensitive detector includes a transducer crystal mounted in bridge-like configuration on pair of spaced piers connected by at least one flexible beam member. The transducer crystal and electrodes may be connected to circuitry for producing indications of respiration and heart rate. The circuitry blocks detection of chest motion substantially coincident with the impulses associated with heartbeat to inhibit erroneous indications of respiration caused by chest motion due to heartbeat. The circuitry also may block small, single polarity signals to inhibit erroneous indications of respiration caused by muscle noise.

29 Claims, 12 Drawing Figures

RESPIRATION AMPLIFIER AND FILTERS

RESPIRATION AND HEART RATE MONITORING APPARATUS

BACKGROUND OF THE DISCLOSURE

The present invention relates to a respiration and heartbeat monitoring system employing a highly sensitive chest motion transducer and associated amplification and filter circuits. The invention is particularly well suited to the monitoring of respiration and heart rate in infants, although the invention may also be used in monitoring adults and animals.

Apnea or the transient cessation of respiration is a leading cause of death in infants. This malady is known to occur during sleep. Constant monitoring of the infant permits prompt detection of apnea and timely corrective action. Unfortunately, in infants normal respiration in sleep is characterized by extremely small chest movements. Detection of these movements and distinguishing them from heartbeat, associated vascular movements or muscle noise has proven difficult.

It is known in the prior art to measure respiration, and other body parameters characterized by mechanical movement, with piezoelectric transducers mechanically coupled to the body. Such systems are shown in U.S. Pat. No. 2,658,505 to Sheer, U.S. Pat. No. 3,782,368 to Reibold, and U.S. Pat. No. 4,185,621 to Morrow.

The Morrow and Sheer patents disclose mountings for piezoelectric crystals for measuring vascular blood flow parameters. The Reibold patent discloses a transducer for measuring respiration employing a large piezoelectric crystal of disc-like geometry bonded directly to a slightly larger metallic disc. Reibold attaches bending arms to the disc so that the arms extend outward from the chest. The arms secures them to ends of the discontinuous chest belt. The belt apparently couples chest expansion forces to the crystal and holds the discs adjacent the chest wall.

However, the Reibold device is not well suited to detection of small chest movements such as occur in respiration in infants.

Accordingly, it is an object of the present invention to provide a sensitive respiration transducer for monitoring respiration in infants.

It is another object of the present invention to provide sensitive respiration transducer employing a small, inexpensive piezoelectric crystal.

It is another object of the present invention to provide a respiration transducer which may be held against the chest of the subject by a relatively flat belt which overlies the transducer.

It is another object of the present invention to provide a sensitive respiration transducer for detecting chest wall flexure beneath the transducer.

Apnea may occur without immediate cessation of heartbeat or so-called "muscle noise" which is small muscle contractions or twitches not indicative of respiration. In such circumstances an extremely sensitive respiration transducer might produce erroneous indications of continued respiration due to detection of chest movements associated with heartbeat, vascular movements or muscle noise. In addition, such movements could distort normal respiration rates measured by such a sensitive transducer.

Accordingly, it is a further object of the present invention to provide a patient monitoring system employing a sensitive respiration transducer, which provides for the inhibiting of erroneous respiration indications caused by heartbeat, vascular movements and muscle noise.

These and other objects and features will be apparent from the written description, read with the associated drawings and claims.

SUMMARY OF THE INVENTION

An apparatus of an embodiment of the present invention includes a respiration detector having an elongated, flexible or elastically deformable beam member and a crystal transducer attached to the beam member on spaced piers in a bridge-like configuration. Longitudinal axes of the crystal transducer and beam member are adapted to be held generally parallel to an outer surface of chest wall of a patient. Bending stresses are transmitted to the crystal transducer during respiration. The crystal transducer is adapted to produce electrical signals responsive to the bending stresses applied to it as an indication of respiration.

The respiration detector and electrocardiograph electrodes may be held against the chest of the patient by a belt which overlies the respiration detector. The electrocardiograph electrodes produce signals responsive to electrical activity associated with the heartbeat of the patient.

The respiration transducer and electrocardiograph electrodes may be electrically connected to monitoring circuitry by means of a cable. The monitoring circuit produces an indication of heart rate from electrical signals from the electrodes and an indication of respiration rate from electrical signals from the transducer. The monitoring circuitry may include filter circuits for inhibiting detection of signals produced by the transducer crystal occurring substantially simultaneously with the signals from the electrodes to thereby inhibit erroneous indications of respiration caused by chest motion due to heartbeat. The filter circuits may also inhibit detection of single polarity signals characteristic of muscle noise. These filter circuits permit the use of a highly sensitive respiration detector and a highly sensitive amplifier in the monitoring circuit.

Such a highly sensitive respiration sensing detector may be provided by coupling motion of an elongated flexible beam member to longitudinal ends of a piezoelectric crystal by means of a pair of spaced pier members.

More particularly, in one embodiment of the present invention, a means for applying bending forces to the piezoelectric crystal may include a first rigid pier and a second rigid pier, both having principal surfaces adapted to be disposed generally parallel to the outer surface of the chest of the patient. The first and second piers may be arranged in spaced relationship to define a gap therebetween. First and second flexible beams may be attached to the piers so that the beams both bridge the gap between the piers and so that the beams are arranged in spaced parallel relation. The crystal may be located between the first and second beams and bridge the gap between the piers. A flexible belt may be employed to encircle the chest of the patient, and, together with the beams and piers, apply a bending stress to the piezoelectric crystal in response to chest expansion during respiration.

In another embodiment the respiration sensing detector may comprise a base member adapted for location adjacent the chest of the subject. The base member is elastically deformable from a rest configuration in response to chest movement. First and second pier members may be attached at spaced locations along a longitudinal axis of the base member to define a gap between the pier members. A piezoelectric crystal transducer may be provided having opposite ends attached to each pier member so that the transducer spans the gap between the pier members and so that bending stresses developed in the base member during respiration are transmitted to the ends of the transducer to produce an electrical signal.

Opposite end portions of the pier members may be bonded to the base member, and portions of the pier members adjacent the gap may be free to deflect away from the base member in response to chest movements during respiration.

Advantageously, to reduce the size and cost of the transducer crystal and provide high sensitivity, the length of the flexible member along its longitudinal axis is selected so that it is substantially greater then the length of the transducer crystal spanning the gap between the pier members. This permits the use of a small transducer crystal whose longest dimension lies along the longitudinal axis of the base member.

In another preferred embodiment of the present invention, a respiration transducer signal amplifier may be provided for amplifying signals produced by a respiration detector such as described above. An electronic switch, such as an FET, may be provided for blocking the amplified transducer signal responsive to the receipt of signals from the electrocardiograph electrodes. Additional circuits may eliminate signals characteristic of muscle noise by filtering out signals which do not have positive and negative going components. This inhibits erroneous respiration indications due to heartbeat and muscle noise.

In another preferred embodiment of the present invention the monitoring circuit may further comprise a respiration rate measuring circuit including a capacitor, biasing circuitry for continually changing the charge on the capacitor and circuitry for coupling the FET switch to the capacitor for charging or discharging the capacitor responsive to a transducer signal indicating a chest motion due to respiration. A comparator circuit compares the charge on the capacitor to a reference voltage and produces an indication if the delay between respiration signals exceeds a preselected time. The reference voltage may be selected to provide a desired delay between the receipt of the previous respiration signal and the initiation of an alarm indication.

DETAILED DESCRIPTION

The present invention relates to systems designed to monitor heart and respiration rates of adults and infants. Newly born infants have extremely small chest movement during sleep and, therefore, extremely sensitive detectors are required to monitor their respiration. According to the teachings of the present invention, the required sensitivity is obtained by the combination of a highly sensitive respiration detector, high sensitivity amplification circuitry, and heart rate and muscle noise filtering circuits, for elimination of erroneous respiration indications. Additional filter circuitry, in both respiration transducer indicator circuits and heart rate indicator circuits, inhibits erroneous signals caused by electrical noise. An alarm system is coupled to the indicator circuits to provide audible and visible signals when respiration and/or heartbeat has ceased or when an electrical connection to the detectors has been broken.

Referring first to FIGS. 1a through 1d, a first embodiment of a respiration detector 10 will now be described. The detector consists generally of a transducer crystal 12 and a device 14 for applying bending forces to the crystal transducer 12 responsive to chest motion.

In the embodiment shown in FIGS. 1a through 1d, the force applying device 14 consists of a first rigid pier 16 and a second rigid pier 18, each having principal surfaces 20 adapted to be disposed generally parallel to the outer surface 21 of the chest of the patient. The piers 16 and 18 are spaced apart to define a gap 22 between proximate edges 24 of the piers. The piers may be made of a dielectric material or thick, rigid ceramic.

Figure 1A:
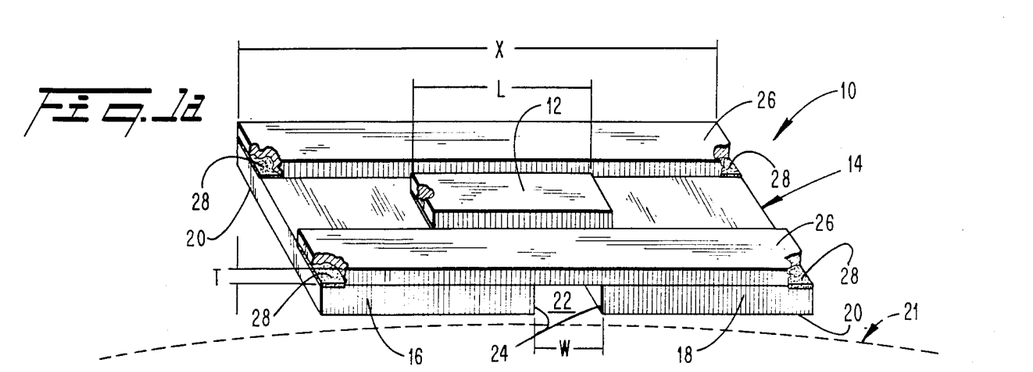
FIG. 1a is a pictorial view of a double beam respiration detector.

An elongated flexible member may consist of two parallel flexible beams 26. The crystal transducer 12 may be located between the beams 26 and span the gap 22 between the piers 16 and 18.

The beams 26 may be attached to the piers 16/18 at locations 28 at opposite end of the piers. The longitudinal axis of the crystal transducer 12 may be located parallel to the longitudinal axes of the beams 26. Advantageously, the length of the flexible beams, X, may be selected to be at least twice the length of the crystal, L. It may be noted that the length is equal to the length of the entire device 14 shown in FIGS. 1a through 1d. Alternatively, the width W of the gap 22 may be less than one third the length X of the flexible beams. These configurations permit use of a small, thin, sensitive crystal transducer. In a preferred embodiment, beams of suitable flexibility have been constructed from brass 0.032" thick (T), 0.25" wide and 1.75" long (X).

Figure 1B:
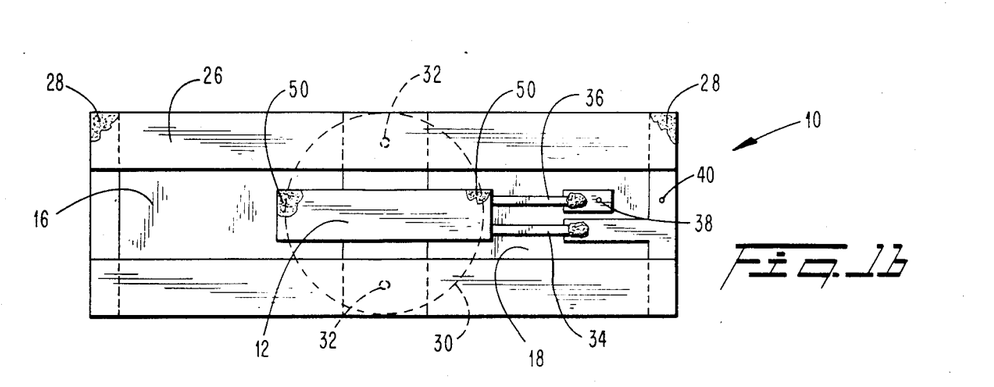
FIG. 1b is a plan view, in partial phantom, of a double beam respiration detector with grounding electrode.
Figure 1C:
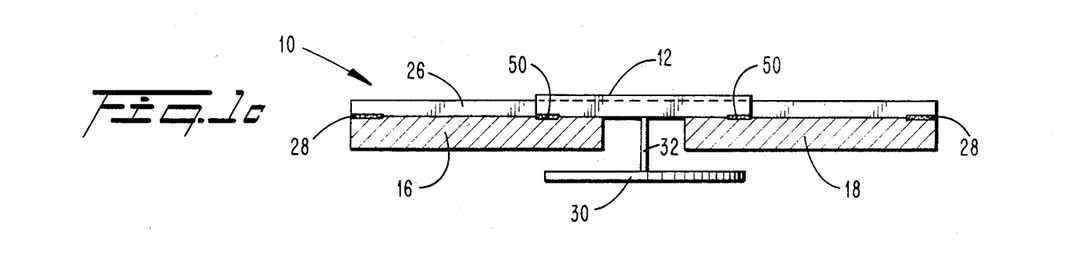
FIG. 1c is a side view of the device of FIG. 1b.

FIGS. 1b and 1c show the attachment of a grounding electrode 30 to the respiration detector. The electrode is used in conjunction with the heart rate monitoring circuits discussed below.

Rigid members 32 may be employed to attach the grounding electrode to the flexible beams 26. The electrode and rigid members 32 may facilitate coupling of bending stresses to the transducer crystal 12.

Electrical connections may be made to the transducer crystal and grounding electrodes by means of copper conductors on one of the rigid piers. As shown best in FIG. 1b, two copper conductors 34 and 36 may be provided on the pier 18. These conductors provide an electrical output signal from the transducer crystal 12 and may be attached at points 38 and 40 to electrical cables leading to a monitoring circuit. The conductor 34 may also be electrically connected to the flexible beams 26, and, thereby, electrically connected through the members 32 to the electrode 30. This conductor path may be selected as the electrical ground for the system.

Figure 1D:
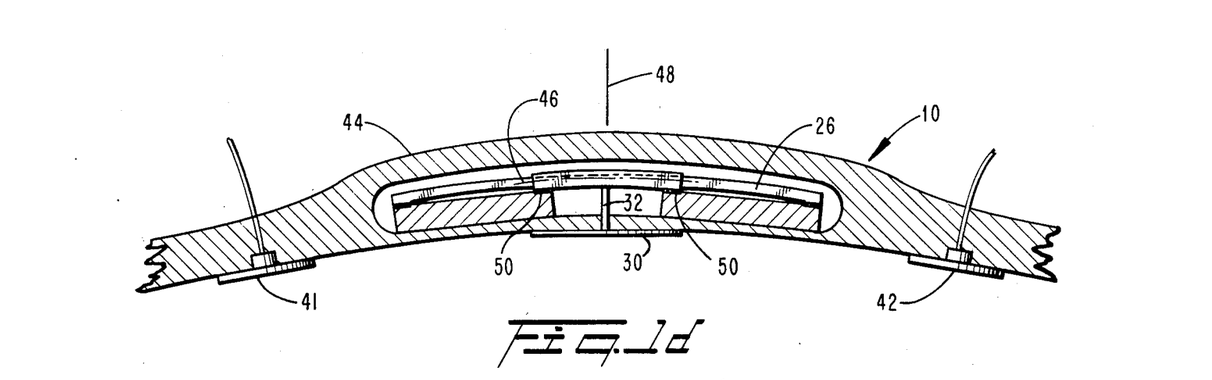
FIG. 1d shows the device of FIG. 1b incorporated into a respiration and heart rate sensor including heart rate monitoring electrodes.

The operation of the respiration detector and its integration into the monitoring system may be better described with reference to FIG. 1d. FIG. 1d shows the relative placements of the grounding electrode 30 and two electrocardiogram electrodes 41 and 42.

FIG. 1d also shows the location of the transducer crystal assembly within a flexible belt 44. In operation, the belt 44 may be positioned to encircle the chest of the patient. Bending forces are applied to the crystal 12, causing its longitudinal axis 46 to bend or deflect slightly from a straight line. Normally, when no stress is placed on the assembly, the longitudinal axis of the crystal transducer would be straight.

Generally speaking the flexible beams 26 are designed to be more flexible than the crystal 12 for deflections in a direction 48 perpendicular to the chest wall. The piers 16 and 18 are designed to be substantially rigid to such deflections. The arrangement may operate to reduce tensile stretching stress on the crystal. As will be apparent from FIG. 1d the straight line distance between bonding points 50 of the crystal 12 to the piers 16/18 shortens slightly as the flexible beams 26 bend in response to stress caused by chest motion. The arrangement also protects the crystal 12 from forces or torques which are not generally perpendicular to the chest wall. This permits use of a relatively smaller, thinner and less expensive transducer crystal 12.

Figure 2A:
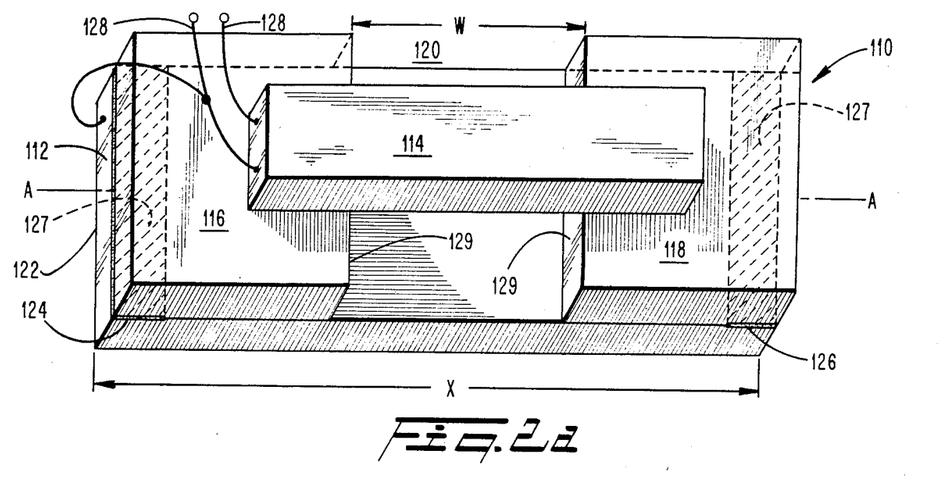
FIG. 2a is a pictorial view, in partial phantom, of a respiration detector having a single base plate.
Figure 2B:
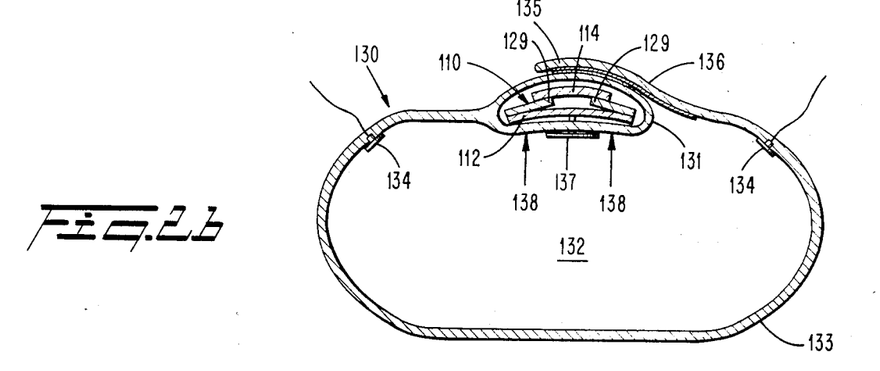
FIGS. 2b and 2c are cross-sectional views of the detector of FIG. 2a incorporated into a respiration and heart rate sensor belt including heart rate monitoring electrodes.
Figure 2C:
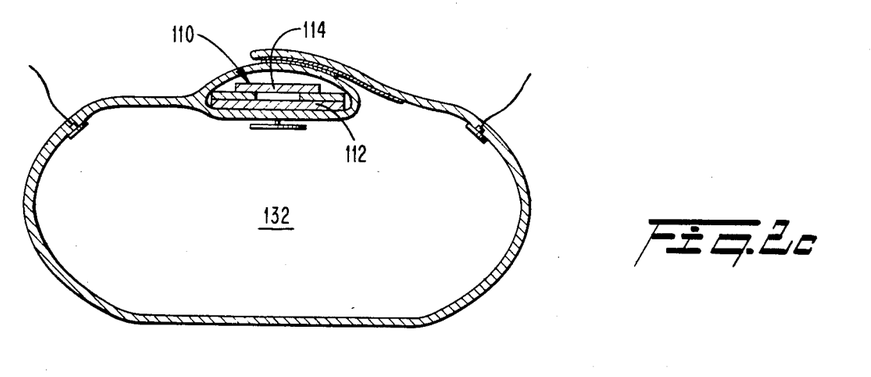

Referring now to FIGS. 2a through 2c an alternate embodiment of a respiration detector, made in accordance with the teachings of the present invention, is indicated generally by the numeral 110. The detector consists of a base member or plate 112 and a transducer crystal 114 supported on the base member by a first pier member 116 and a second pier member 118. As shown in the figure, the pier members 116 and 118 are separated by a central gap 120 which the crystal 114 overlies in a bridge-like or spanning configuration.

The base member 112 may be made of an elastically deformable material such as spring steel. A first major surface 122 of the base member 112 may be held generally parallel to the chest wall of the patient. Opposite end portions 124 and 126 of the base member 112 may be bonded to the first pier member 116 and second pier member 118, respectively. The areas of bonding are indicated by the cross-hatched regions identified by numeral 127.

A longitudinal axis in the plane of the base member 112 is indicated by the line A—A. When the respiration transducer is held against the chest wall of the patient, flexure of the chest wall elastically deforms the base member 112 so that the axis A—A is no longer a straight line. When this occurs, the pier members 116/118 may couple forces developed at longitudinally opposite ends of the base member 112 to end portions of the transducer crystal 114. End portions 129, of the pier members 116/118 may separate from the base plate 112 as the base plate 112 flexes. Care must be taken that tensile stresses on the crystal 114 used in this embodiment do not become sufficiently large to damage the crystal 114.

In embodiments of the present invention a crystal 114 is selected with a length L along the longitudinal axis A—A of about 0.75". The length of the base member 112 (X) may be about 1.75" and the width of the gap 120 (W) may be about 0.25".

With continued reference to FIG. 2a, stress imparted to the transducer crystal 114 produces a voltage across terminals of electrical leads 128. One of the leads may be grounded to the base plate 112 as indicated in the figure. The pier members 116 and 118 may, in a preferred embodiment, be made of dielectric material. In this event, the leads 128 need not be insulated.

The operation of the monitoring system of the present invention may be better understood with reference to the drawings of FIGS. 2b and 2c which show the orientation of components of the detector of FIG. 2a in cross-section at different stages of chest movement during respiration. In FIGS. 2b and 2c a chest belt 130 is shown surrounding a thoracic region 132 of the patient or subject. A portion 131 of the belt 130 encases the respiration detector and a strap portion 133 encircles the thoracic region 132. An end portion 135 of the strap is releasably attached to the portion 131, for example by means of VELCRO strips. This permits the patient to be laid on the opened belt 130, and the portions 135 and 131 adjusted and attached without turning over the patient.

Electrocardiograph electrodes 134 are fixed to the belt 130. Advantageously, the electrodes 134 are thin, dry electrodes, typically about ½ inch in diameter. A grounding electrode 137 may be attached to the respiration detector base plate 112. The electrode surfaces are held snugly against the chest of the patient. This arrangement coupled with a sensitive input amplifier for the ECG electrodes permits the use of the electrodes in a dry condition without the application of conductive paste to the skin of the patient which may cause skin damage.

The respiration transducer 110 is located inside the belt 130 and held in place by the belt walls which provide a smooth belt cover 136 for protection of the respiration transducer 110. In FIG. 2b the respiration sensor 110 is shown in the configuration which would occur during upward expansion or flexure of the chest wall as indicated schematically by the arrows 138. As seen in the figure, adjacent ends 129 of the pier members 116/118 are displaced away from the base member 112 by the movement of the chest wall and exert stress on the piezoelectric crystal 114 producing an electrical signal. In contrast, as shown in FIG. 2c, the base member 112 returns to its undeformed state when the upward flexing forces 138 are removed as during exhalation. In this configuration, the stress on the piezoelectric crystal 114 may be reduced thus changing the electrical output of the transducer 110.

Figure 3:
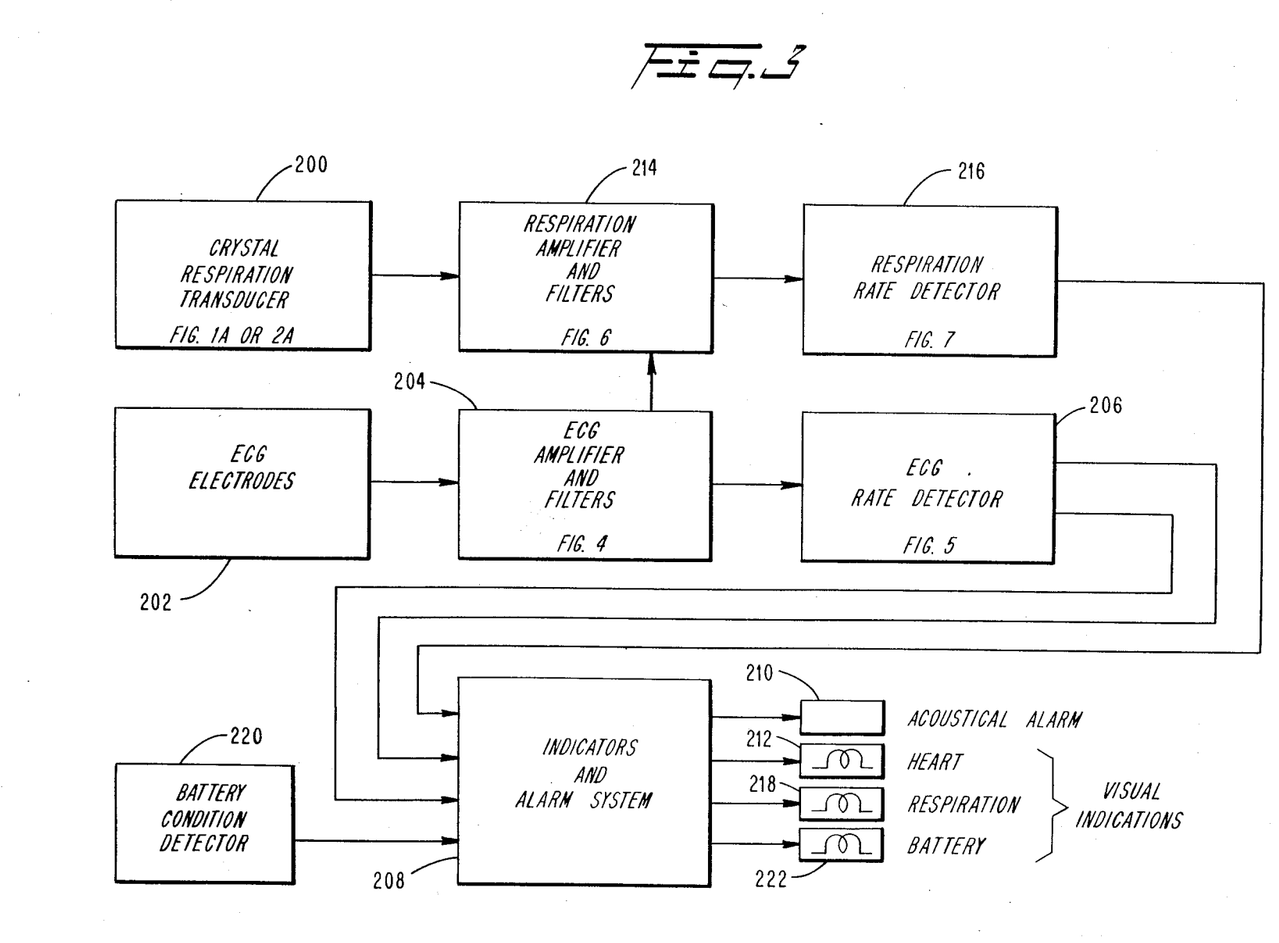
FIG. 3 is a schematic block diagram of the respiration and heart rate monitoring system of the present invention.

FIG. 3 is a schematic block diagram of the respiration and heart rate monitoring system of the present invention. The circuit includes a sensitive crystal respiration transducer 200 such as the transducer shown in FIGS. 1a or 2a. The system also includes ECG electrodes shown schematically as block 202. The crystal respiration transducer 200 and the ECG electrodes 202 are connected to a circuitry package which comprises the remainder of FIG. 3. This connection may be made by means of a single cable. Because the monitoring circuitry constantly monitors signals from the respiration transducer and the electrodes, a loose electrode, broken lead or disconnected cable will be detected by the system as an absence of respiration or heart rate, and an alarm will be produced.

The signals from the ECG electrodes are applied to the ECG amplifier and filters 204, described in greater detail in connection with FIG. 4. The ECG amplifier and filters are characterized by a high input impedance and sufficient sensitivity to allow the use of dry electrodes. An amplified and filtered signal from the ECG amplifier and filters is then applied to a ECG rate detector 206, described in greater detail in connection with FIG. 5. The ECG rate detector is adapted to produce an ECG alarm signal in response to a heart rate abnormality. The ECG alarm signal is communicated to the indicators and alarm system 208. The indicators and alarm system, in turn, activate an acoustical alarm 210 or heartbeat indicator 212.

An output signal of the crystal respiration transducer 200 is applied to the respiration amplifer and filters 214, discussed in greater detail in connection with FIG. 6. In addition, shaped ECG pulses, produced by the ECG amplifier and filter circuit 204, are applied to the respiration amplifier and filter 214. The respiration amplifier and filters circuit has a high input impedance to improve the voltage response of the transducer crystal. The respiration amplifier and filters circuit 214 operates to inhibit detection of signals produced by the crystal respiration transducer occurring substantially simultaneously with signals from the electrocardiograph electrodes, thereby inhibiting erroneous indications of respiration caused by chest motion due to heartbeat.

A filtered respiration signal from the respiration amplifier and filters circuit 214 is applied to the respiration rate detector 216. The respiration rate detector provides an indication of a reduction of respiration rate below a preset threshold. If respiration rate falls below the preset threshold, a signal is applied to the indicators and alarm system 208 which activates a respiration alarm 218. The circuit does not respond to single-polarity signals produced by small muscle movement or noise.

The electrical circuitry is powered by a low voltage battery source to prevent shock hazards and permit the circuitry to be produced in a small, self-contained, portable package. A battery condition indicator circuit 220 is also provided. In the case that the battery voltage falls below a preset level, a signal is transmitted to the indicators and alarm system 208 which subsequently activates the battery alarm indicator 222.

All of the indications produced by the indicator and alarm system may be audible and/or visual indications and provision may be made for short range radio transmission of the signals to remote monitoring stations.

Figure 4:
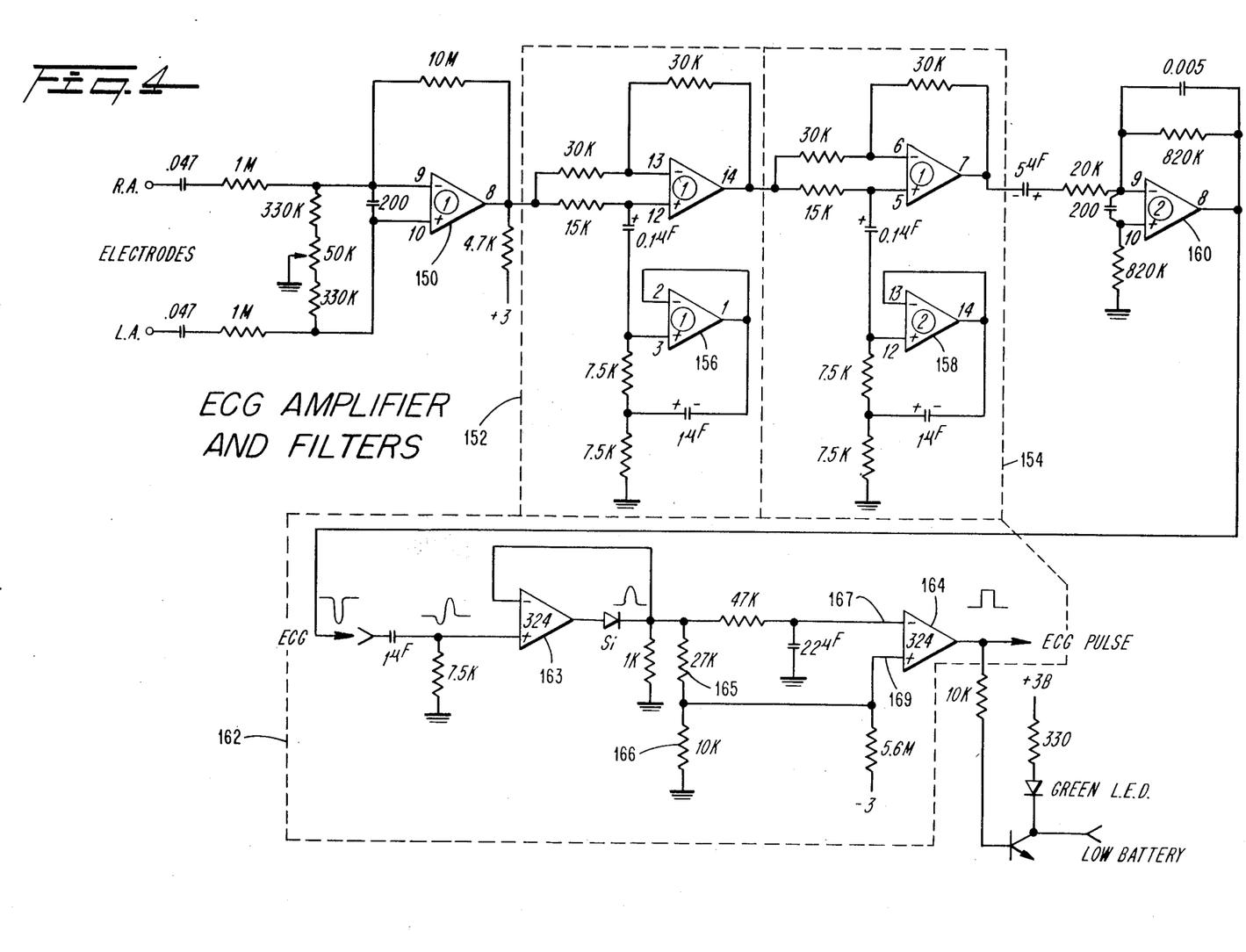
FIGS. 4-7 are schematic diagrams of the circuitry shown more generally in FIG. 3.

FIG. 4 is a schematic circuit diagram of the ECG amplifier and filter circuit 204. The first stage of the circuit includes an amplifier 150 having a high impedance input section. Noise reduction is achieved by the input circuit which increases common mode signal level capabilities.

Two sequential notch filters 152 and 154 are provided for reducing noise, chiefly 60 cycle hum, which may be induced in the system. Each notch filter includes a gyrator based on amplifiers 156 and 158. This circuit arrangement avoids the use of heavy and bulky inductors in the filters.

Amplifier 160 forms the basis of a bandpass filter. An output signal from comparator 160 is subsequently applied to pulse shaping and filtering circuit 162.

The ECG pulse shaping and filtering circuit 162 will now be described in greater detail. An ECG pulse entering the circuit 162 will be predominantly negative as shown in FIG. 4. A rectifier circuit, including a first amplifier 163, transforms the pulse into a positive waveform as shown.

The first amplifier circuit acts as a small signal half-wave rectifier which produces only a positive rectified pulse. Noise signals also will pass through the first amplifier circuit, the noise being predominantly 60 Hz noise which is a primary source of malfunction in monitoring circuits of this type. Oscillatory or sinusoidal type noise signals are in effect filtered in a unique and advantageous way, described below.

The half-wave rectifier will rectify all sinusoidal-like waveforms. Such half-waveforms have a direct current or average value to peak value of 0.32. A comparator circuit including an amplifier 164, operating as a comparator, filters oscillatory or sinusoidal noise signals from ECG pulses. More specifically, a 47k ohm resistor and 22 microfarad capacitor filter the waveform from the rectifier to produce an average dc value and hold an inverting terminal 167 of a second amplifier 164 at that average value. A voltage divider, consisting of a 27k ohm resistor 165 and a 10k ohm resistor 166, may impose about 0.27 times the peak amplitude at a second, non-inverting terminal 169 of the second amplifier 164. When sinusoidal noise is present, the input voltages of the second amplifier are very nearly the same, and the amplifier 164 is biased slightly to keep the amplifier output low when only sinusoidal noise is present.

The ECG pulse output of the rectifier is, typically, a relatively narrow (low duty cycle) pulse. The average value is very small and consequently the voltage at the inverting terminal 167 changes very little (i.e., a few millivolts). However, approximately $\frac{1}{3}$ of the ECG pulse voltage is applied through the voltage divider to the non-inverting terminal 169 which causes the output of the amplifier 164 to go positive during the input ECG pulse.

If the noise amplitude changes, then both input terminal voltages of the amplifier 164 change accordingly and in the same direction. Thus, noise is effectively filtered.

In an alternative embodiment (not shown) the rectifier circuit could be the full-wave type. In such a case the average-to-peak value of sinusoidal waveforms would be 0.64. However, the half-wave rectifier is preferred because the ECG rectified pulse has a smaller average value.

Figure 5:
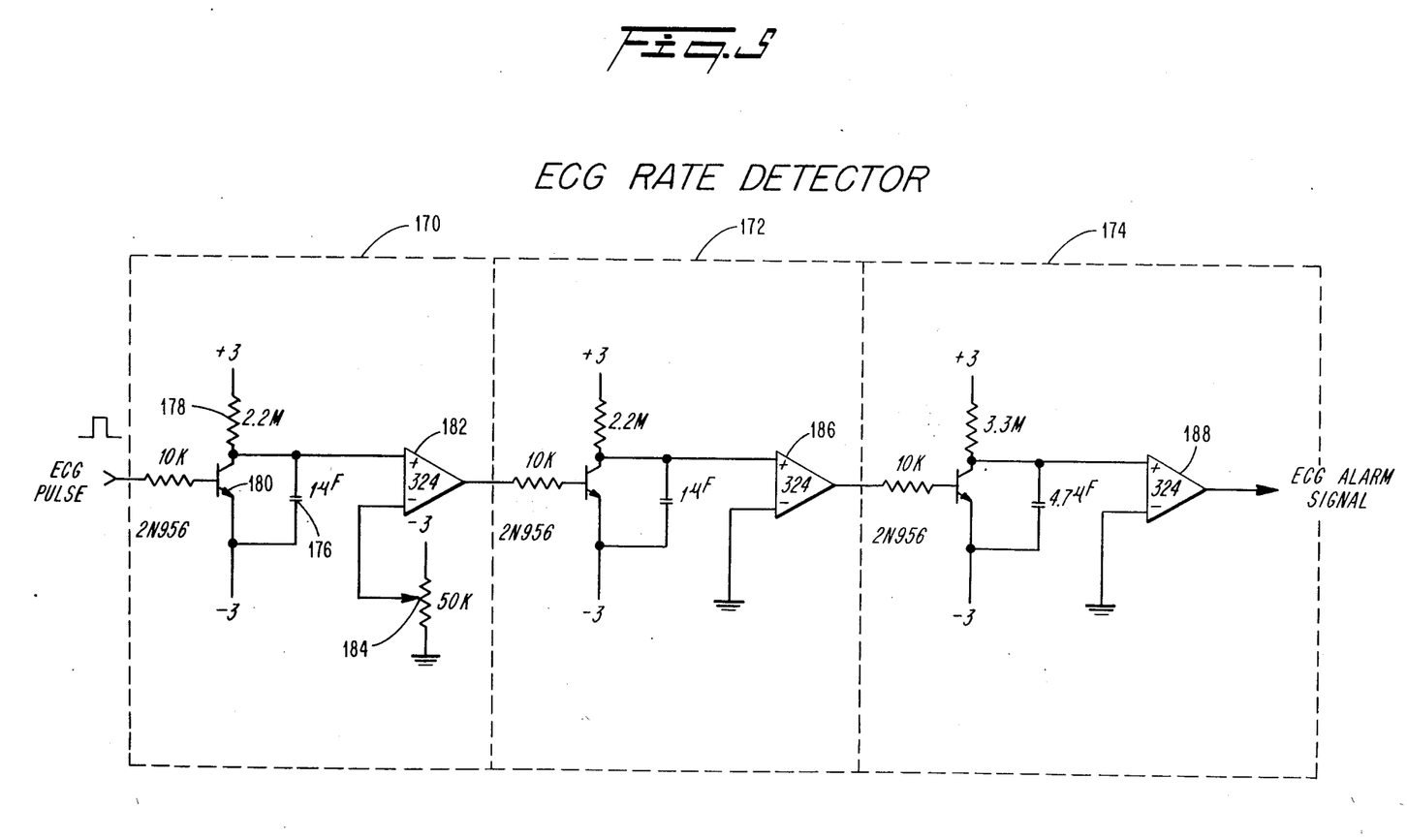
Figure 6:
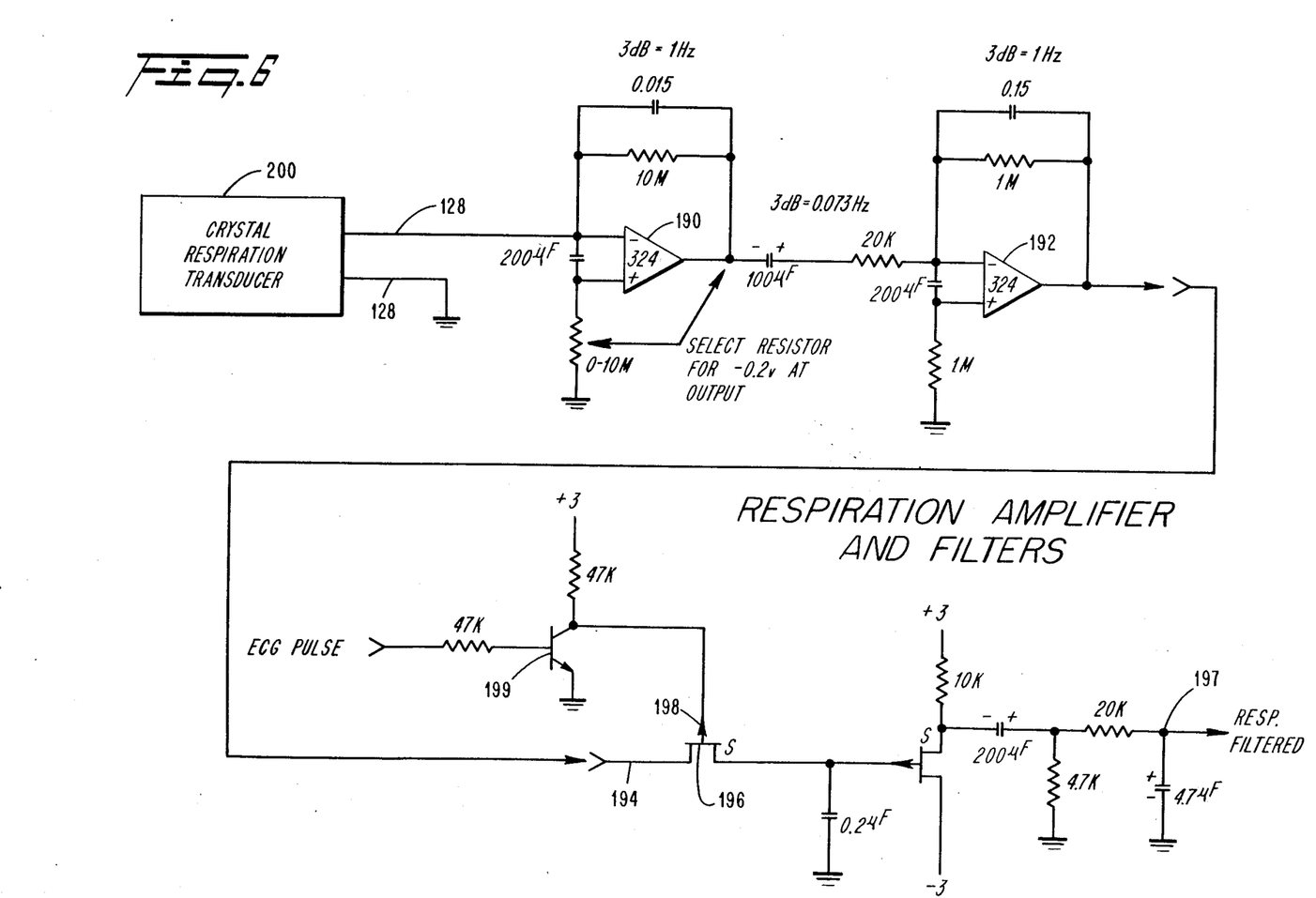

An ECG pulse from the circuit 162 is applied both to the ECG rate detector of FIG. 5 and the respiration amplifier and filters 214 of FIG. 6. Referring first to FIG. 5, the ECG pulse is applied to three delay circuits 170, 172 and 174. In a preferred embodiment of the present invention the ECG rate detector provides an alarm signal if the heart rate does not exceed a preset rate, the rate being selectable (80 BPM, 72 BPM, 65 BPM).

The first delay circuit 170 includes a capacitor 176 which is continuously charged by biasing circuitry including the plus and minus 3 volt power supply voltage and the resistor 178. Receipt of an ECG pulse causes transistor 180 to conduct, thereby discharging the capacitor 176. If a ECG pulse is not received, the capacitor 176 will continue to charge until a voltage level is reached at the positive input terminal of comparator 182 which will produce a pulse. The pulse is applied to the second time delay circuit 172. The voltage which must be reached across capacitor 176 in order to enable the comparator 182 is determined by the setting of potentiometer 184. The setting of the potentiometer determines the bias voltage applied to the negative terminal of the comparator 182, and, therefore, the threshold level at which an indicator pulse is produced. The delay circuits 172 and 174 operate in a similar manner except that the voltage on the negative terminal of the amplifiers 186 and 188 is held at ground. The delay circuit 172 acts as a memory circuit to prevent an ECG alarm in the event of heart beat skips.

As discussed above the ECG alarm signal from the ECG rate detector is subsequently applied to the indicators and alarm system 208.

FIG. 6 is a detailed schematic circuit diagram of the respiration amplifier and filters circuit 214 showing the connection of the crystal respiration transducer 200. The input circuitry associated with the operational amplifier 190 provides a high impedance to maximize voltage response from the crystal. Noise, predominately 60 cycle noise, inherent in the use of such a high impedance is reduced by the use of two filter stages employing the operational amplifiers 190 and 192.

An amplified transducer signal at the output of operational amplifier 192 is applied to an input terminal of an electronic switch such as the drain terminal 194 of field effect transistor 196. ECG pulses from the ECG amplifier and filter circuit 204 are applied to the gate terminal 198 of the field effect transistor via transistor 199.

In operation, the transistor switch inhibits detection of signals produced by the crystal respiration transducer occurring substantially simultaneously with signals from the electrocardiograph electrodes, thereby inhibiting erroneous indication of respiration caused by chest motion due to heartbeat. A filtered respiration signal, which appears at terminal 197 is applied to the respiration rate detector 216 which will now be described in connection with FIG. 7.

Figure 7:
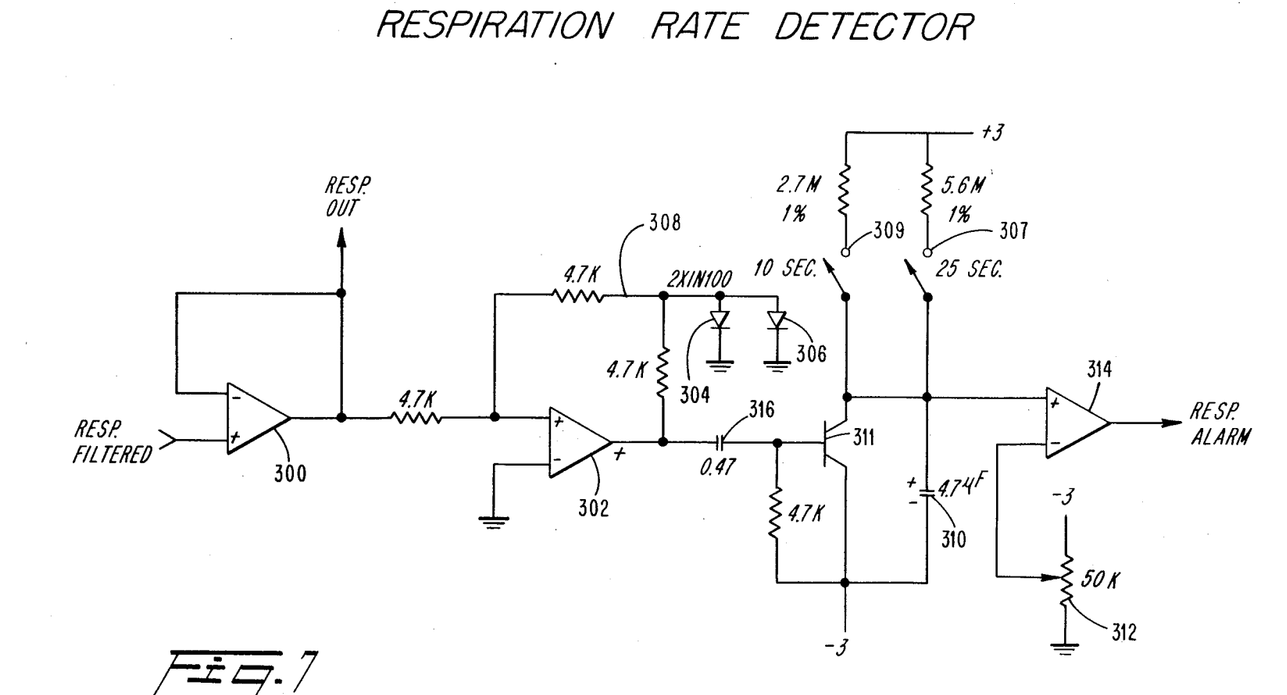

In the respiration rate detector circuit of FIG. 7, a first amplifier 300 receives the filtered respiration signal from the circuit of FIG. 6. The first amplifier 300 is a voltage follower, or buffer, amplifier. A second amplifier 302, receiving an output signal of the first amplifier, has a gain of approximately 10. Two diodes 304 and 306 are provided in the feedback path 308 and cause the amplifier 302 to have Schmitt circuit hysteresis property, where preferably the hysteresis limits are approximately ±20 millivolts. A capacitor 310 is continuously charged by a bias voltage selected by switches 307 or 309. The selection determines the time delay of the circuit. A transistor 311 is provided to discharge the capacitor 310 in response to receipt of a respiration signal.

If the patient stops breathing there can be small muscle movements which produce an output voltage from the breathing transducer. These signals are predominately single polarity whereas a normal breathing signal has positive and negative going components. These small muscle noise signals may disrupt the delay circuit timing action and thus prevent the production of an alarm signal at appropriate times. Circuitry is provided to inhibit such erroneous indications of respiration.

For signals at the output of the second amplifier 302 which are less than 20 millivolts, the Schmitt action clamps the output at plus or minus 20 millivolts and the timing capacitor 310 begins charging. When the capacitor reached a predetermined voltage determined by the setting of variable resistor 312, the comparator 314 produces an alarm signal.

If the signal from the amplifier 300 makes a positive or a negative excursion greater than 20 mv in amplitude and remains positive or negative the Schmitt trigger action clamps the output voltage and the timing capacitor continues to charge toward an alarm signal voltage because the coupling capacitor 316 will not pass the steady signal from the Schmitt trigger.

Thus to prevent the timing comparator circuit from producing an alarm signal, a signal produced by respiration, which has positive and negative excursions, must be present. Such a signal produces an output pulse which causes the transistor 311 to conduct, thereby discharging the timing capacitor 310.

Output alarm signals from the respiration rate detector circuit of FIG. 7 may be applied to the indicator and alarm system 208 to provide visible or audible alarm indication when respiration rate falls below a predetermined rate.

The principles, preferred embodiments and modes of operation of the present invention have been described in the foregoing specification. The invention which is intended to be protected herein, however, is not to be construed as limited to the particular forms disclosed, since these are to be regarded as illustrative rather then restrictive. Variations and changes may be made by those skilled in the art without departing from the spirit of the invention.

We claim:

1. A respiration sensing apparatus adapted to be held adjacent the chest of a patient and convert movements of the chest during respiration to an electrical signal, comprising:
   a first, rigid pier having a principal surface adapted to be disposed generally parallel to the outer surface of the chest of the patient;
   a second, rigid pier having a principal surface adapted to be disposed generally parallel to the outer surface of the chest of the patient, said second pier being separated from the first pier to define a gap therebetween;
   a first elongated flexible beam bridging the gap between the first and second piers;
   a second, elongated flexible beam bridging the gap between the first and second piers, and lying in spaced, parallel relation to the first beam;
   a piezoelectric crystal, located between the first and second beams and bridging the gap between the first and second beams; and
   a flexible belt adapted to encircle the chest of the patient, said beams, piers and crystal being attached to said belt, and said belt together with said beams and piers, apply a bending stress to said piezoelectric crystal in response to expansion of the chest during respiration.

2. The respiration sensing apparatus of claim 1 wherein the beams extend longitudinally over the piers and are attached to the piers at locations displaced from the gap between the piers.

3. The respiration sensing apparatus of claim 2 wherein the crystal is elongated in a direction parallel to the beams and wherein the crystal is substantially shorter in its direction of elongation than the beams.

4. The respiration sensing apparatus of claim 3 wherein the beams and crystal lie generally in the same plane, and wherein the beams are attached to the piers only at portions of the principal surfaces of the piers displaced from the gap between the piers.

5. The respiration sensing apparatus of claim 3 further comprising an electrode adapted for location against the chest of the patient and attached to at least one of said flexible beams by a member extending from the electrode to a location or a portion of the beam bridging the gap between the piers.

6. A respiration sensing apparatus comprising:
   a crystal which produces an electrical signal responsive to chest wall action of a patient during respiration; and
   a means for applying bending forces to said crystal responsive to chest wall action of the patient comprising:
      first and second substantially parallel flexible members disposed in spaced relationship relative to each other adapted to be held so that the longitudinal axes of said first and second substantially parallel flexible members are substantially parallel to the chest wall of the patient, and adapted to be flexed by a chest wall action of the patient during respiration so that a varying curvature is imposed on said longitudinal axes;
      substantially rigid first and second pier members including proximate edges disposed in spaced relationship relative to each other to cooperatively form a gap therebetween, attached to said first and second substantially parallel flexible members;
   said crystal being attached to said first and second pier members to span said gap cooperatively formed between said first and second pier members disposed in substantially parallel relationship relative to said first and second substantially parallel flexible members.

7. The respiration sensing apparatus of claim 6 wherein said first and second substantially parallel flexible members are attached to said first and second pier members at locations separated from said proximate edges of said first and second pier members by a distance substantially greater than said gap between said first and second pier members.

8. The respiration sensing apparatus of claim 6 wherein said crystal is disposed between said first and second substantially parallel flexible members.

9. The respiration sensing apparatus of claim 6 wherein the length of said first and second substantially flexible members is substantially greater than the length of said crystal spanning said gap cooperatively formed between said first and second pier members.

10. The respiration sensing apparatus of claim 9 wherein the length of said first and second substantially parallel flexible members is greater than three times the length of said gap cooperatively formed between said first and second pier members.

11. The respiration sensing apparatus of claim 9 wherein the length of said first and second substantially parallel flexible members is greater than twice the length of said crystal.

12. The respiration sensing apparatus of claim 6 wherein each of said first and second substantially parallel flexible members comprises a beam of resilient metal and said crystal comprises a piezoelectrical crystal.

13. The respiration sensing apparatus of claim 6 further comprising a flexible belt adapted to encircle the chest of the patient, said flexible members, pier members and crystal being attached to said belt, and, said belt together with said first and second substantially parallel flexible members and said first and second pier members apply a bending stress to said crystal in response to expansion of the chest of the patient during respiration.

14. The respiration sensing apparatus of claim 6 further comprising an electrode adapted for location against the chest of the patient and attached to said first and second substantially parallel flexible members by a substantially rigid member extending from said electrode to said first and second substantially parallel flexible members.

15. A respiration sensing apparatus comprising:
   a base member adapted for location adjacent the chest of a patient and being elastically deformable in response to chest movements;
   first and second pier members attached to said base member at locations along the longitudinal axis of said base member such that said first and second pier members are spaced apart;
   a piezoelectric element having opposite ends thereof attached to said first and second pier members so that said piezoelectric element spans said space between said first and second pier members and so that bending stresses developed in said base member due to chest movement are transmitted to the ends of said piezoelectric element to produce an electrical signal; and
   opposite end portions of each of said first and second pier member being bonded to said base members and portions of said first and second pier members adjacent said space are capable of deflecting away from said base member in response to chest movement during respiration.

16. The respiration sensing apparatus of claim 15 wherein the length of said base member along the longitudinal axis is substantially greater than the length of said piezoelectric element spanning said space between first and second pier members.

17. The respiration sensing apparatus of claim 15 wherein said opposite end portions of each of said first and second pier member are bonded adjacent to said opposite ends of said base members.

18. The respiration sensing apparatus of claim 15 wherein said space between said first and second pier members is located centrally relative to said base member.

19. The respiration sensing apparatus of claim 15 further comprising a belt which contains said base member, first and second pier members and piezoelectric element; said belt retaining said base member adjacent the chest of the patient.

20. The respiration sensing apparatus of claim 15 wherein said base member comprises a spring plate; each of said first and second pier members comprises a dielectric material; and said piezoelectric element comprises a piezoelectric crystal.

21. A respiration and heart rate monitoring apparatus for a patient comprising:
   a respiration transducer including a piezoelectric crystal and first and second flexible beams disposed in substantially parallel spaced relationship relative to each other, each of said first and second flexible beams having a principal plane adapted to be held substantially parallel to a surface of the chest wall of a patient and a pair of substantially rigid members each attached to one opposite end portion of said substantially parallel first and second flexible beams and one opposite end portion of said piezoelectric crystal, said piezoelectric crystal being disposed between said substantially parallel first and second flexible beams, said substantially rigid members being adapted to transmit bending stress to said piezoelectric crystal thereby producing electric signals responsive to motion of the chest;

electrodes adapted to be in electrical communication with the chest wall of the patient which produce signals responsive to the heartbeat of the patient;

belt means for holding said respiration transducer and said electrodes against the chest of the patient; and circuit means connected to said respiration transducer and said electrodes for producing an indication of heart rate and respiration rate, said circuit means including filter circuit means for inhibiting detection of signals produced by said piezoelectric crystal occurring substantially simultaneous with the signals from the electrodes, to thereby inhibit erroneous indications of respiration caused by chest motion due to heartbeat.

22. The respiration and heart rate monitoring apparatus of claim 21 wherein said circuit means includes:
    an amplifier means for amplifying said signals produced by said piezoelectric crystal; and
    switch means for blocking said amplified signals, said switch means being responsive to said signals from said electrodes; and
    circuit means for blocking low-level amplified signals which are not both positive and negative going.

23. The respiration and heart rate monitoring apparatus of claim 22 further comprising an electrocardiograph signal processing circuit for amplifying and shaping signals from said electrodes and wherein said switch means is a field effect transistor having a gate terminal to which an amplified and shaped electrocardiograph signal is applied.

24. The respiration and heart rate monitoring apparatus of claim 22 further comprising a respiration rate measuring circuit including:
    a capacitor;
    biasing means for continuously changing the charge on the capacitor;
    means for coupling said switch means to said capacitor for changing the charge on said capacitor responsive to a transducer signal indicating chest motion due to respiration; and
    comparator means for comparing the charge on said capacitor to a reference voltage.

25. The respiration and heart rate monitoring apparatus of claim 22 wherein each of said first and second flexible beams comprises a substantially rectangular planar member elastically deformable from a planar configuration by chest motion; and
    each said substantially rigid member comprises a rectangular block of dielectric material bonded to said substantially rectangular planar members at longitudinally opposite ends of said substantially rectangular planar members.

26. The respiration and heart rate monitoring apparatus of claim 21 wherein said circuit means includes means for filtering sinusoidal noise from input signals received from said electrodes adapted to be in electrical communication with the chest wall, said filtering means including a comparator, means for applying an average voltage derived from said input signal to one input terminal of said comparator and voltage divider means for applying a predetermined fraction of the peak voltage of the input signal to a second input terminal of said compartor, said predetermined fraction being selected so that said comparator is inhibited from producing an erroneous indication of heartbeat in response to sinusoidal noise.

27. A respiration sensing apparatus comprising:
    a crystal which produces an electrical signal responsive to chest wall action of a patient during respiration; and
    a means for applying bending forces to said crystal responsive to chest wall action of the patient comprising:
        a flexible element including first and second substantially parallel flexible members disposed in spaced relationship relative to each other adapted to be held so that the longitudinal axes of said first and second substantially parallel flexible members are substantially parallel to the chest wall of the patient, and adapted to be flexed by chest wall action of the patient during respiration so that a varying curvature is imposed on said longitudinal axes;
        substantially rigid first and second pier members disposed in spaced relationship relative to each other to cooperatively form a gap therebetween, attached to said first and second substantially parallel flexible members;
    said crystal being attached to said first and second pier members to span said gap cooperatively formed between said first and second pier members disposed in substantially parallel relationship relative to said first and second substantially parallel flexible members.

28. A respiration sensing apparatus comprising:
    an elongated crystal which produces an electrical signal responsive to chest wall action of a patient during respiration; and
    a means for applying bending forces to said crystal responsive to chest wall action of the patient comprising:
        an elongated flexible member adapted to be held so that the longitudinal axis of said elongated flexible member is substantially parallel to the longitudinal axis of said elongated crystal and the chest wall of the patient, and adapted to be flexed by the chest wall action of the patient during respiration so that a varying curvature is imposed on said longitudinal axis of said elongated flexible member;
        substantially rigid first and second pier members disposed in spaced relationship relative to each other to cooperatively form a gap therebetween, attached to said elongated flexible member;
        opposite end portions of said first and second pier members being bonded to said elongated flexible member and the portions of said first and second pier members adjacent said gap are capable of deflecting away from said elongated flexible member in response to chest movement during respiration;
    said elongated crystal being attached to said first and second pier members to span said gap cooperatively formed therebetween.

29. A respiration sensing apparatus comprising:
    a crystal which produces an electrical signal responsive to chest wall action of a patient during respiration; and
    a means for applying bending forces to said crystal responsive to chest wall action of the patient comprising:

a flexible member adapted to be held so that the longitudinal axis of said flexible member is substantially parallel to a chest wall of the patient, and adapted to be flexed by chest wall action of the patient during respiration so that a varying curvature is imposed on said longitudinal axis;

substantially rigid first and second pier members disposed in spaced relationship relative to each other to cooperatively form a gap therebetween, attached to said flexible member;

said crystal and said flexible member being attached to said first and second pier members to span said gap cooperatively formed therebetween;

the longitudinal axis of said crystal being substantially parallel to the longitudinal axis of said flexible member;

said crystal and said flexible member being disposed in the same plane when said respiration sensing apparatus is unstressed.

* * * * *